United States Patent
Chang et al.

(10) Patent No.: US 9,625,581 B2
(45) Date of Patent: Apr. 18, 2017

(54) THREE-DIMENSIONAL (3D) EMITTING APPARATUS

(71) Applicant: Daegu Gyeongbuk Institute of Science and Technology, Daegu (KR)

(72) Inventors: Pyung Hun Chang, Seoul (KR); Gezgin Erkin, Izmir (TR)

(73) Assignee: Daegu Gyeongbuk Institute of Science and Technology, Daegu (KR)

( * ) Notice: Subject to any disclaimer, the term of this patent is extended or adjusted under 35 U.S.C. 154(b) by 0 days.

(21) Appl. No.: 14/541,090

(22) Filed: Nov. 13, 2014

(65) Prior Publication Data

US 2015/0285915 A1   Oct. 8, 2015

(30) Foreign Application Priority Data

Apr. 7, 2014 (KR) ........................ 10-2014-0041395

(51) Int. Cl.

| | | |
|---|---|---|
| *G01B 11/30* | (2006.01) | |
| *G01S 17/89* | (2006.01) | |
| *B33Y 30/00* | (2015.01) | |
| *B29C 67/00* | (2017.01) | |
| *G01B 11/00* | (2006.01) | |
| *B33Y 50/00* | (2015.01) | |

(Continued)

(52) U.S. Cl.

CPC .......... *G01S 17/89* (2013.01); *B29C 67/0085* (2013.01); *B29C 67/0088* (2013.01); *B33Y 30/00* (2014.12); *B33Y 50/00* (2014.12); *G01B 11/002* (2013.01); *G01S 7/4817* (2013.01); *G01S 17/42* (2013.01); *B29C 67/0059* (2013.01); *B33Y 50/02* (2014.12)

(58) Field of Classification Search

CPC ......... G01S 17/89; G01B 11/00; G01B 5/004; A61B 19/00; B25J 18/04

See application file for complete search history.

(56) References Cited

U.S. PATENT DOCUMENTS

| | | | |
|---|---|---|---|
| 8,303,575 B2 * | 11/2012 | Rodriguez Y Baena | ............................ A61B 19/22 606/1 |
| 2005/0166413 A1 * | 8/2005 | Crampton | .............. B25J 13/088 33/503 |
| 2012/0045308 A1 * | 2/2012 | Kremerman | ............. B25J 9/042 414/744.3 |

FOREIGN PATENT DOCUMENTS

| | | | |
|---|---|---|---|
| JP | 5165527 | 4/2010 | |
| JP | 2010094882 | * 4/2010 | ............... B41J 2/01 |

(Continued)

OTHER PUBLICATIONS

Office Action cited in KR 10-2014-0041395, dated Apr. 7, 2014.
Office Action cited in KR 10-2014-0041395, dated Jan. 22, 2015.

*Primary Examiner* — Tarifur Chowdhury
*Assistant Examiner* — Jamil Ahmed
(74) *Attorney, Agent, or Firm* — Marshall, Gerstein & Borun LLP

(57) ABSTRACT

A three-dimensional (3D) emitting apparatus includes a table on which an object is to be disposed, a robot arm to perform a task on the object, an emitting member provided at an end portion of the robot arm, and a controller to control an operation of the robot arm or a position of the emitting member, wherein the table and the robot arm may move relatively in a vertical or horizontal direction, the emitting member may move along a trajectory of rotation of the robot arm, and the trajectory of rotation may be provided in a form of a concentric sphere having a center at which a target point is disposed.

18 Claims, 5 Drawing Sheets

(51) Int. Cl.
  *G01S 17/42*    (2006.01)
  *G01S 7/481*    (2006.01)
  *B33Y 50/02*    (2015.01)

(56) References Cited

FOREIGN PATENT DOCUMENTS

| | | | | |
|---|---|---|---|---|
| JP | 2010094882 A | * | 4/2010 | ................ B41J 2/01 |
| KR | 2011-0102759 | | 9/2011 | |
| KR | 1020120057549 A | * | 5/2012 | ............. A61B 18/00 |
| KR | 10-2013-0004446 A | | 1/2013 | |
| KR | 10-0004446 | | 1/2013 | |
| KR | 1020130004446 A | * | 1/2013 | ............. G01B 11/24 |
| KR | 20130038101 A | | 4/2013 | |
| KR | 10-1339009 | | 12/2013 | |

\* cited by examiner

THREE-DIMENSIONAL (3D) EMITTING APPARATUS

CROSS-REFERENCE TO RELATED APPLICATION

This application claims the benefit of Korean Patent Application No. 10-2014-0041395, filed on Apr. 7, 2014, in the Korean Intellectual Property Office, the disclosure of which is incorporated herein by reference.

BACKGROUND

1. Field of the Invention

Embodiments of the present invention relate to a three-dimensional (3D) emitting apparatus, and more particularly, to a 3D emitting apparatus that may be aimed at a target point accurately and rapidly.

2. Description of the Related Art

In general, a machine performing a motion similar to a motion of a human using an electrical or magnetic action is referred to as a robot. With the recent development of control technology, robots are utilized in various fields. The robots include, for example, a housekeeper robot at a home, a service robot in a public area, a transfer robot in a production filed, and a worker assistance robot. Such robots perform tasks using a manipulator produced to be capable of performing a motion similar to a motion of an arm or a hand by electrical or mechanical mechanism.

Such robots may be used for various applications, for example, a three-dimensional (3D) scanner or a 3D printer. The 3D scanner refers to a device that measures a 3D shape of an object and obtains 3D shape data. An example of the 3D scanner is a contact 3D scanner that measures an overall curved shape of an object by measuring spatial coordinates of each point while in contact with the object along a surface of the object.

The 3D printer is technology that manufactures an object by outputting successive layers of a material similar to a two-dimensional (2D) printer and laminating the output layers. The 3D printer may produce an object rapidly based on digitized drawing data and thus, is mainly used to produce a prototype sample. For example, Korean Patent Application No. 2011-0102759, filed on Oct. 8, 2011, discloses "High resolution dental 3D printer by using multiple projection systems".

SUMMARY

An aspect of the present invention provides a three-dimensional (3D) emitting apparatus that may be aimed at a target point rapidly and accurately through relative movements of a robot arm and a table.

Another aspect of the present invention also provides a 3D emitting apparatus that may increase a directivity with respect to a target point through easy control.

Still another aspect of the present invention also provides a 3D emitting apparatus that may reduce an overall weight by reducing a number of drive members through a compact design.

Yet another aspect of the present invention also provides a 3D emitting apparatus that may be configured in a form of a cyberknife, a 3D scanner, or a 3D printer.

According to an aspect of the present invention, there is provided a 3D emitting apparatus including a table on which an object is to be disposed, a robot arm to perform a task on the object, an emitting member provided at an end portion of the robot arm, and a controller to control an operation of the robot arm or a position of the emitting member. The table and the robot arm may move relatively in a vertical or horizontal direction, the emitting member may move along a trajectory of rotation of the robot arm, and the trajectory of rotation may be provided in a form of a concentric sphere having a center at which a target point is disposed.

A plurality of robot arms may be provided, emitting members corresponding to a number of the robot arms may be provided, and the plurality of emitting members may face an identical target point. The robot arm may include a plurality of link members and a plurality of drive members, the plurality of link members may be disposed on concentric spheres having an identical center, and extension lines of axes of the drive members may be positioned at the center.

The robot arm may be disposed above or below the table, and the 3D emitting apparatus may be configured in a form of a cyberknife that emits radiation from the emitting member toward the object.

The 3D emitting apparatus may further include an image sensor to convert light emitted from the emitting member and reflected by the object into an electrical image signal, and a data processor to generate a 3D image by combining a plurality of images received from the image sensor. The 3D emitting apparatus may be configured in a form of a 3D scanner that acquires a 3D shape of the object.

The object may be provided using a fluid material including an ink, an ultraviolet ray may be emitted from the emitting member, and the 3D emitting apparatus may be configured in a form of a 3D printer that irradiates the ultraviolet ray toward the object to harden the object.

The robot arm may include a first central member, a first link member to rotate on a longitudinal axis of the first central member, a first drive member disposed at one end of the first link member to transmit a torque to the first link member, a second link member connected to another end of the first link member to rotate on a first axis, and a second drive member disposed between the first link member and the second link member to transmit a torque to the second link member.

The robot arm may further include a third link member connected to a portion of the first central member, the portion differing from a portion to which the first link member is connected, to rotate on the longitudinal axis of the first central member, a third drive member disposed at one end of the third link member to transmit a torque to the third link member, a fourth link member connected to another end of the third link member to rotate on a second axis, and a fourth drive member disposed between the third link member and the fourth link member to transmit a torque to the fourth link member.

The robot arm may further include a second central member disposed on an axis identical to the longitudinal axis of the first central member and spaced apart from the center by a distance corresponding to a distance between the first central member and the center, a fifth link member to rotate on a longitudinal axis of the second central member, a fifth drive member disposed at one end of the fifth link member to transmit a torque to the fifth link member, a sixth link member connected to another end of the fifth link member to rotate on a third axis, and a sixth drive member disposed between the fifth link member and the sixth link member to transmit a torque to the sixth link member.

The robot arm may further include a seventh link member connected to a portion of the second central member, the portion differing from a portion to which the fifth link member is connected, to rotate on the longitudinal axis of the second central member, a seventh drive member disposed at one end of the seventh link member to transmit a torque to the seventh link member, an eighth link member connected to another end of the seventh link member to rotate on a fourth axis, and an eighth drive member disposed between the seventh link member and the eighth link member to transmit a torque to the eighth link member.

The longitudinal axis of the first central member, the longitudinal axis of the second central member, the first axis, the second axis, the third axis, and the fourth axis may be positioned at the center.

The first axis, the second axis, the third axis, and the fourth axis may be formed to be perpendicular to tangential directions of end portions of the first link member, the second link member, the third link member, the fourth link member, the fifth link member, the sixth link member, the seventh link member, and the eighth link member.

The first link member and the second link member may be disposed farther away from the center than the third link member and the fourth link member, and the fifth link member and the sixth link member may be disposed farther away from the center than the seventh link member and the eighth link member.

When the third link member is disposed between the first link member and the second link member, lengths of the third link member and the fourth link member may be shorter than a length of the first link member.

The third link member and the fourth link member may be disposed closer to the center than the second link member, and the fourth link member may be disposed closer to the center than the third link member.

When the seventh link member is disposed between the fifth link member and the sixth link member, lengths of the seventh link member and the eighth link member may be shorter than a length of the fifth link member.

The seventh link member and the eighth link member may be disposed closer to the center than the sixth link member, and the eighth link member may be disposed closer to the center than the seventh link member.

The emitting member may be disposed to be perpendicular to tangential directions of end portions of the second link member, the fourth link member, the sixth link member, and the eighth link member.

The 3D emitting apparatus may further include a position adjustment element to adjust a position of the table.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Figure 1:
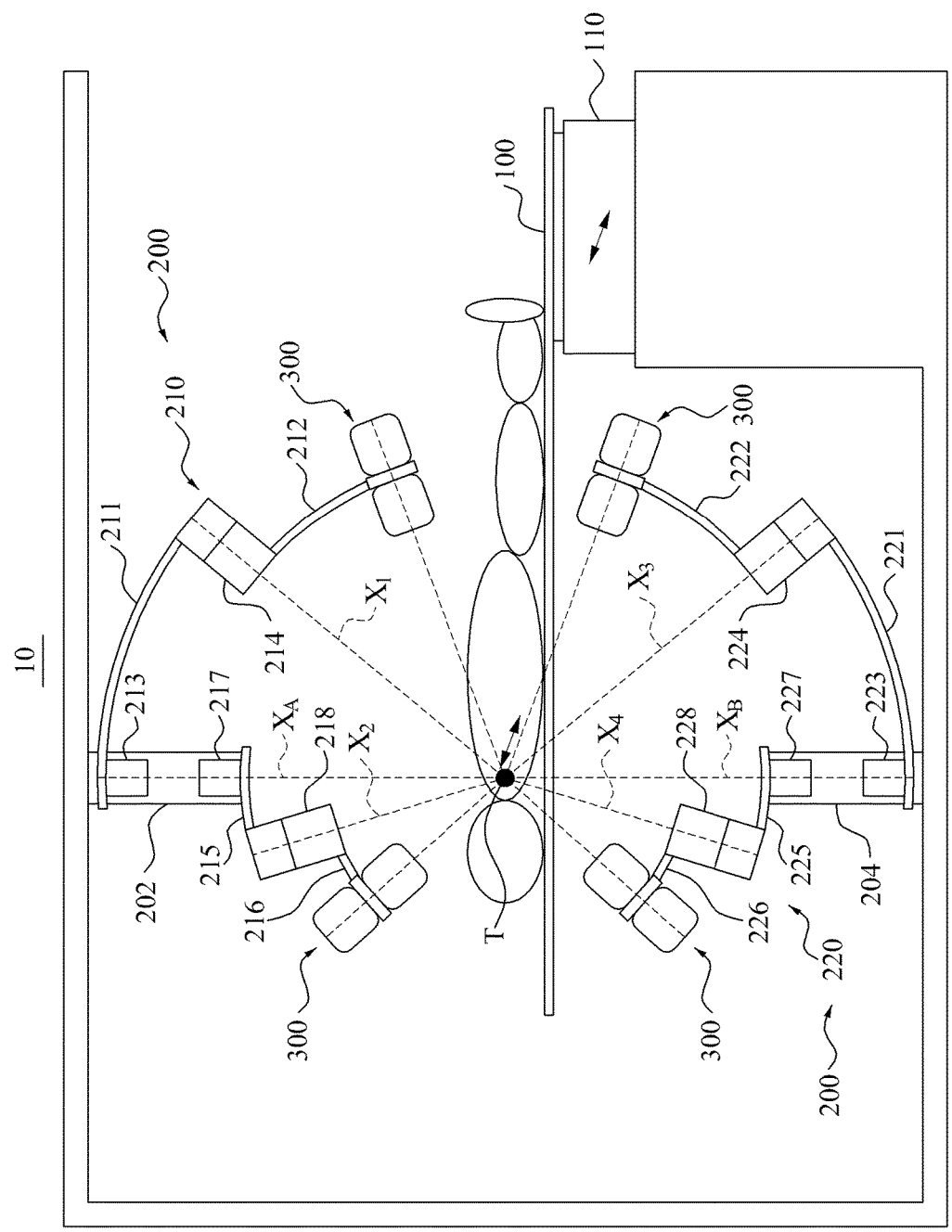
FIG. 1 illustrates a three-dimensional (3D) emitting apparatus used as a cyberknife according to an embodiment of the present invention.

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

A three-dimensional (3D) emitting apparatus according to an embodiment of the present invention may include a table on which an object is to be disposed, a robot arm to perform a task with respect to the object, an emitting member disposed at an end portion of the robot arm, and a controller to control an operation of the robot arm or a position of the emitting member.

The table and the robot arm may move relatively in a vertical or horizontal direction, the emitting member may move along a trajectory of rotation of the robot arm, and the trajectory of rotation may be provided in a form of a sphere having a center at which a target point is disposed.

A plurality of robot arms may be provided, emitting members corresponding to a number of the robot arms may be provided, and the plurality of emitting members may face an identical target point.

The robot arm may include a plurality of link members and a plurality of drive members, the plurality of link members may be disposed on concentric spheres having an identical center, and extension lines of axes of the plurality of drive members may be positioned at the center.

The foregoing describes a general configuration of a 3D emitting apparatus, and the 3D emitting apparatus may be applicable to various fields. For example, the 3D emitting apparatus may be applicable to a cyberknife, a 3D scanner, or a 3D printer. Hereinafter, a 3D emitting apparatus applied to a cyberknife, a 3D scanner, and a 3D printer will be described in detail.

Figure 2:
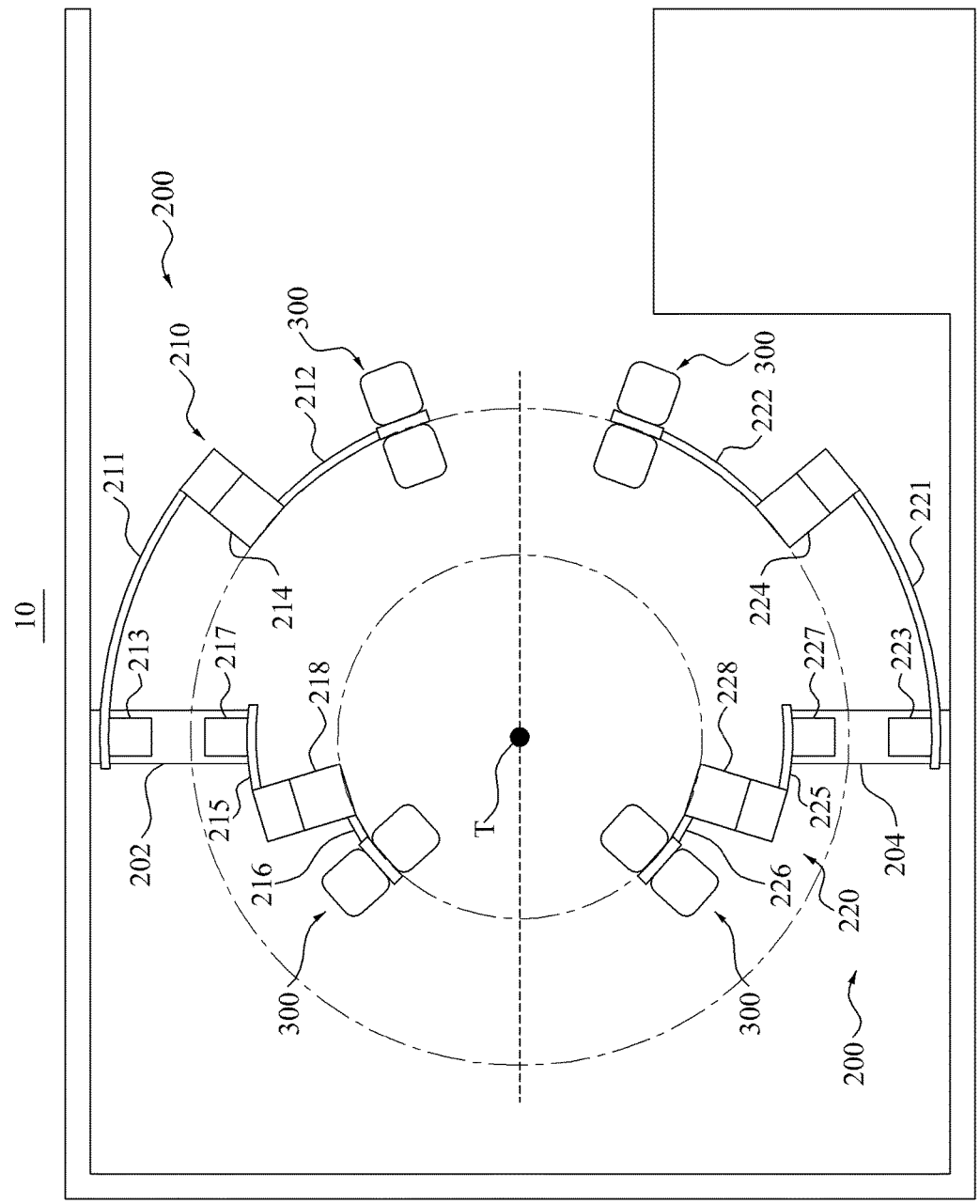
FIG. 2 illustrates a disposition of robot arms in a 3D emitting apparatus according to an embodiment of the present invention.

FIG. 1 illustrates a 3D emitting apparatus 10 used as a cyberknife according to an embodiment of the present invention, and FIG. 2 illustrates a disposition of robot arms in the 3D emitting apparatus 10 according to an embodiment of the present invention. Referring to FIG. 1, the 3D emitting apparatus 10 may include a table 100, a robot arm 200, and a controller (not shown). An object may be disposed on the table 100.

When the 3D emitting apparatus 10 is used as a cyberknife, the object may be a cancer patient requiring radiation therapy or a tumor removing surgery. In this example, a target point T may be a treatment or surgery area, for example, a position of a tumor.

A position adjustment element 110 may be disposed at the table 100 to adjust a position of the table 100.

As shown in FIG. 1, when the position adjustment element 110 moves in a direction of an arrow, the table 100 may also move in the direction of the arrow.

The position of the table 100 or the object may be freely adjusted and thus, the target point T may be repositioned. In detail, the table 100 may move in a direction vertical or horizontal to the ground. Accordingly, the table 100 and the robot arm 200 may move relatively in the vertical or horizontal direction.

When the table 100 is fixed, the position of the object may be fixed. By moving the robot arm 200, an emitting position of an emitting member 300 or a position at which radiation is emitted from the emitting member 300 may be moved relatively with respect to the table 100.

The object may be repositioned to the target point T by relatively moving the table 100 with respect to the robot arm 200 through the position adjustment element 110, and the emitting member 300 may move to face the target point T. Thus, the emitting member 300 provided at the robot arm 200 may be efficiently aimed at the target point T of the object disposed on the table 100. The robot arm 200 may be disposed above or below the table 100. The robot arm 200 may include an upper robot arm 210 and a lower robot arm 220. The emitting member 300 may be provided at an end portion of each of the upper robot arm 210 and the lower robot arm 220. Thus, a number of robot arms 200 may be equal to a number of emitting members 300.

Referring to FIG. 2, the upper robot arm 210 and the lower robot arm 220 may be disposed within trajectories on spheres having an identical center, for example, the identical target point T.

The emitting member 300 of the upper robot arm 210 and the emitting member 300 of the lower robot arm 220 may move in response to rotation of the upper robot arm 210 and the lower robot arm 220. Thus, the emitting members 300 may move along spherical trajectories of the upper robot arm 210 and the lower robot arm 220. The emitting members 300 may be disposed to face the identical target point T.

Accordingly, radiation emitted from the emitting member 300 provided on the upper robot arm 210 and radiation emitted from the emitting member 300 provided on the lower robot arm 220 may be concentrated on a single singular point. The emitting members 300 may be easily aimed at the target point T.

The upper robot arm 210 and the lower robot arm 220 may be disposed to be spaced apart from each other based on the table 100. Through such a disposition of the upper robot arm 210 and the lower robot arm 220, the upper robot arm 210 and the lower robot arm 220 may operate incoherently, and a mutual collision between the upper robot arm 210 and the lower robot arm 220 may be prevented.

The upper robot arm 210 and the lower robot arm 220 may respectively include a plurality of link members and a plurality of drive members. For example, the upper robot arm 210 may include a first link member 211, a second link member 212, a third link member 215, and a fourth link member 216.

The first link member 211 may be connected to a first central member 202 to rotate on a longitudinal axis $X_A$ of the first central member 202.

The first central member 202 may be disposed in a vertical direction on an inner side of a frame provided on an outer side of the 3D emitting apparatus 10, for example, a medical robot.

The first link member 211 may be disposed on a sphere having a center at the target point T, and provided in a form of an arc.

The first link member 211 may have a longer length than the second link member 212, the third link member 215, and the fourth link member 216, and be disposed farthest away from the target point T.

The second link member 212 may be connected to another end of the first link member 211.

The second link member 212 may rotate based on a first axis $X_1$.

The first axis $X_1$ may be angled with respect to the longitudinal axis $X_A$ of the first central member 202.

The third link member 215 may be connected to a portion of the first central member 202, the portion differing from a portion to which the first link member 211 is connected.

The third link member 215 may rotate on the longitudinal axis $X_A$ of the first central member 202. For example, the first link member 211 may be connected to an upper portion of the first central member 202, and the third link member 215 may be connected to a lower portion of the first central member 202.

The fourth link member 216 may be connected to another end of the third link member 215. The fourth link member 216 may rotate on a second axis $X_2$.

The second axis $X_2$ may be angled with respect to the longitudinal axis $X_A$ of the first central member 202.

The upper robot arm 210 may further include a first drive member 213, a second drive member 214, a third drive member 217, and a fourth drive member 218.

The first drive member 213 may be included in the first central member 202. The first drive member 214 may transmit a torque to the first link member 211.

The second drive member 214 may transmit a torque to the second link member 212.

The second drive member 214 may be disposed to face the target point T along the first axis $X_1$.

Similar to the first drive member 213, the third drive member 217 may be included in the first central member 202. The third drive member 217 may transmit a torque to the third link member 215.

The first drive member 213 and the third drive member 217 may be provided integrally or separately. For example, when the first drive member 213 and the third drive member 217 are provided separately, the first link member 211 and the third link member 215 may rotate in different directions or at different velocities.

The fourth drive member 218 may transmit a torque to the fourth link member 216. The fourth drive member 218 may be disposed to face the target point T along the second axis $X_2$. In this example, extension lines of the longitudinal axis $X_A$ of the first central member 202, the first axis $X_1$, and the second axis $X_2$ may be positioned at the target point T.

The emitting member 300 provided at the second link member 212 and the emitting member 300 provided at the fourth link member 216 may be provided in a vertical direction with respect to the second link member 212 and the fourth link member 216, and disposed to face the target point T.

In addition to the extension lines of the longitudinal axis $X_A$ of the first central member 202, the first axis $X_1$, and the second axis $X_2$, the emitting members 300 and the drive members 213, 214, 217, and 218 may also be disposed to face the target point T. Thus, radiations may be emitted or irradiated from the emitting members 300 toward the target point T. The lower robot arm 220 may include a fifth link member 221, a sixth link member 222, a seventh link member 225, and an eighth link member 226.

The fifth link member 221 may rotate on a longitudinal axis $X_B$ of a second central member 204.

The second central member 204 may be disposed in a vertical direction on the inner side of the frame provided on the outer side of the 3D emitting apparatus 10, for example, the medical robot.

The first central member 202 and the second central member 204 may be provided on an identical axis. The second central member 204 may be spaced apart from the target point T by a distance corresponding to a distance between the first central member 202 and the target point T.

The fifth link member 221 may be disposed on a sphere having a center at the target point T, and provided in a form of an arc.

The sixth link member 222 may be connected to another end of the fifth link member 221. The sixth link member 222 may rotate on a third axis $X_3$.

The third axis $X_3$ may be angled with respect to the longitudinal axis $X_B$ of the second central member 204.

The seventh link member 225 may be connected to a portion of the second central member 204, the portion differing from a portion to which the fifth link member 221 is connected. The seventh link member 225 may rotate on the longitudinal axis $X_B$ of the second central member 204. For example, the fifth link member 221 may be connected to a lower portion of the second central member 204, and the seventh link member 225 may be connected to an upper portion of the second central member 204.

The eighth link member 226 may be connected to another end of the seventh link member 225. The eighth link member 226 may rotate on a fourth axis $X_4$.

The fourth axis $X_4$ may be angled with respect to the longitudinal axis $X_B$ of the second central member 204.

The lower robot arm 220 may further include a fifth drive member 223, a sixth drive member 224, a seventh drive member 227, and an eighth drive member 228.

The fifth drive member 223 may be included in the second central member 204. The fifth drive member 223 may transmit a torque to the fifth link member 221.

The sixth drive member 224 may transmit a torque to the sixth link member 222. The sixth drive member 224 may be disposed to face the target point T along the third axis $X_3$.

Similar to the fifth drive member 223, the seventh drive member 227 may be included in the second central member 204. The seventh drive member 227 may transmit a torque to the seventh link member 225.

The fifth drive member 223 and the seventh drive member 227 may be provided integrally or separately. For example, when the fifth drive member 223 and the seventh drive member 227 are provided separately, the fifth link member 221 and the seventh link member 225 may rotate in different directions or at different velocities.

The eighth drive member 228 may transmit a torque to the eighth link member 226. The eighth drive member 228 may be disposed to face the target point T along the fourth axis $X_4$. In this example, extension lines of the longitudinal axis $X_B$ of the second central member 204, the third axis $X_3$, and the fourth axis $X_4$ may be positioned at the target point T.

The emitting member 300 provided at the sixth link member 222 and the emitting member 300 provided at the eighth link member 226 may be provided in a vertical direction with respect to the sixth link member 222 and the eighth link member 226, and disposed to face the target point T.

In addition to the extension lines of the longitudinal axis $X_B$ of the second central member 204, the third axis $X_3$, and the fourth axis $X_4$, the emitting members 300 and the drive members 223, 224, 227, and 228 may also be disposed to face the target point T. Thus, radiations may be emitted or irradiated from the emitting members 300 toward the target point T.

In the drawings, the upper robot arm 210 and the lower robot arm 220 are provided in similar or identical forms. However, the forms of the upper robot arm 210 and the lower robot arm 220 are not limited thereto. The upper robot arm 210 and the lower robot arm 220 may be provided in any form in which the emitting member 300 provided at the upper robot arm 210 and the emitting member 300 provided at the lower robot arm 220 are disposed to face the identical target point T.

To prevent a mutual collision when the plurality of link members 211, 212, 215, 216, 221, 222, 225, and 226 of the upper robot arm 210 and the lower robot arm 220 rotates simultaneously, the plurality of link members 211, 212, 215, 216, 221, 222, 225, and 226 may be disposed as follows.

The first link member 211 and the second link member 212 may be disposed farther away from the target point T than the third link member 215 and the fourth link member 216, and the fifth link member 221 and the sixth link member 222 may be disposed farther away from the target point T than the seventh link member 225 and the eighth link member 226.

When the third link member 215 is disposed between the first link member 211 and the second link member 212, the length of the third link member 215 may be shorter than the length of the first link member 211, and the fourth link member 216 may be disposed closer to the target point T than the second link member 212.

When the seventh link member 225 is disposed between the fifth link member 221 and the sixth link member 222, the length of the seventh link member 225 may be shorter than the length of the fifth link member 221, and the eighth link member 226 may be disposed closer to the target point T than the sixth link member 222.

The 3D emitting apparatus 10 may further include the controller (not shown). Operations of the drive members 213, 214, 217, 218, 223, 224, 227, and 228 or the positions of the emitting members 300 may be easily controlled by the controller.

The controller may operate the drive members 213, 214, 217, 218, 223, 224, 227, and 228 selectively or simultaneously to dispose the emitting members 300 to face the target point T.

The controller may control the operations of the drive members 213, 214, 217, 218, 223, 224, 227, and 228 to adjust rotation velocities or rotation directions of the link members 211, 212, 215, 216, 221, 222, 225, and 226.

Further, the controller may control an operation of the position adjustment element 110 to relatively move the table 100 and the robot arm 200. Although not shown in detail in the drawings, angle adjustment elements may be provided at the emitting members 300 or end portions of the second link member 212, the fourth link member 216, the sixth link member 222, and the eighth link member 226 to move the emitting members 300 at a relatively small angle.

The angle adjustment elements may be useful when a minute angle adjustment is required after the emitting members 300 are aimed at the target point T by means of the drive members 213, 214, 217, 218, 223, 224, 227, and 228.

All axes of the drive members 213, 214, 217, 218, 223, 224, 227, and 228 may face the target point T. Thus, the emitting members 300 may be continuously aimed at the target point T while the link members 211, 212, 215, 216, 221, 222, 225, and 226 are rotating. The foregoing may be achieved based on a structural disposition of the link members 211, 212, 215, 216, 221, 222, 225, and 226 and the drive members 213, 214, 217, 218, 223, 224, 227, and 228. In particular, radiations may be emitted in a state in which the link members 211, 212, 215, 216, 221, 222, 225, and 226 of the robot arms 210 and 220 are stationary. Thus, radiations may not be emitted while the link members 211, 212, 215, 216, 221, 222, 225, and 226 of the robot arms 210 and 220 are moving to subsequent emission points.

However, when the robot arms 210 and 220 include the plurality of link members 211, 212, 215, 216, 221, 222, 225, and 226, radiations may be emitted in a state in which remaining link members are stationary while one of the link members 211, 212, 215, 216, 221, 222, 225, and 226 is moving. Thus, a treatment or surgery time may be reduced.

In addition, when the plurality of robot arms 210 and 220 is provided, the treatment or surgery time may be reduced more efficiently. As described above, when the 3D emitting apparatus 10 is used as a cyberknife, a treatment or surgery time may be reduced, and a tumor at an inaccessible position may be removed efficiently through an excellent directivity. A robot arm may be added or detached, whereby a degree of freedom may increase or decrease and a flexible design may be achieved.

Hereinafter, the 3D emitting apparatus 10 used as a 3D scanner will be described.

Figure 3:
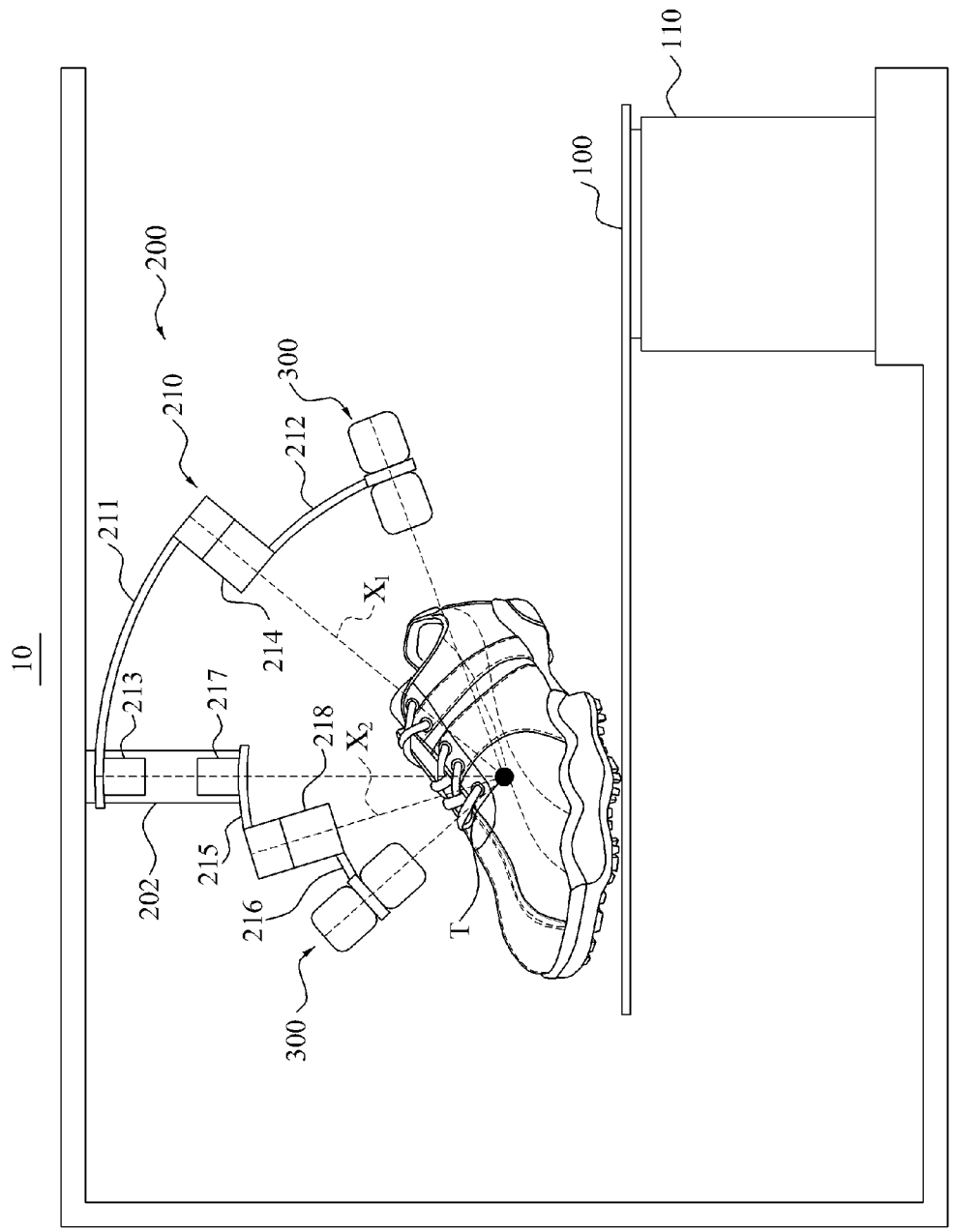
FIG. 3 illustrates a 3D emitting apparatus used as a 3D scanner according to an embodiment of the present invention.

FIG. 3 illustrates the 3D emitting apparatus 10 used as a 3D scanner according to an embodiment of the present invention.

Referring to FIG. 3, when the 3D emitting apparatus 10 is used as a 3D scanner, an object may be provided using an item to be scanned. The object may be disposed on the table 100, and light such as, for example, visible rays or lasers may be emitted from the emitting member 300. Although not illustrated in detail, the 3D emitting apparatus may further include an image sensor to convert light reflected by the object into an electrical image signal, and a data processing apparatus to generate a 3D image by combining a plurality of images received from the image sensor.

The emitting member 300 of the 3D emitting apparatus 10 may be aimed at the object and emit light toward the object. Although FIG. 3 illustrates the robot arm 200 disposed only above the object, it is obvious that the robot arm 200 may also be disposed below the object. Light may be reflected by the object, and the reflected light may be converted into an electrical image signal. By combining electrical image signals, a 3D image of the object may be generated. In this example, the 3D emitting apparatus 10 may be easily aimed at the object and reduce a time used to scan the object through its structure and operation. In addition, the 3D emitting apparatus 10 may be provided in a relatively simple structure and a small volume, the 3D scanner may be stored in a relatively small space.

In an example, the 3D emitting apparatus 10 may be used as a 3D printer. When the 3D emitting apparatus 10 is used as a 3D printer, an object may be provided using a fluid material including an ink. The object may be disposed on the table 100, and ultraviolet rays may be emitted from the emitting member 300.

As shown in FIG. 3, the robot arm 200 of the 3D emitting apparatus 10 may be disposed above the object.

When ultraviolet rays are irradiated on the fluid material, a portion of the fluid material exposed to the ultraviolet rays may be hardened. By iteratively performing this process, the fluid material may be laminated on the table 100. By removing an unhardened portion from the laminated fluid material using chemical and physical methods, a desired hardened 3D shape may be left.

When ultraviolet rays are irradiated on the fluid material in a desired pattern using a projector, a portion of the fluid material exposed to the ultraviolet rays may be hardened. By iteratively performing this process, the fluid material may be laminated on the table 100.

When an ink is dropped on the table 100 using an inkjet head and ultraviolet rays are irradiated on the ink, a portion of the ink exposed to the ultraviolet rays may be hardened. By iteratively performing this process, the fluid material may be laminated on the table 100.

Accordingly, an object as shown in FIG. 3 may be printed by the 3D printer. When the 3D emitting apparatus 10 as described above is used, more accurate emitting may be performed on the fluid material, whereby a more elaborate 3D shape may be obtained. In addition, a time used to aim at the fluid material may be reduced, whereby a time used for 3D printing may be reduced.

Hereinafter, a kinematical analysis on a structure of the 3D emitting apparatus 10 will be described in detail. The following may be expressed based on forward kinematics.

$$x = f(\theta) \qquad \text{[Equation 1]}$$

In the Equation 1, $\theta$ denotes a joint angle, and x denotes a location and direction of an end-effector. Coordinates of an emitting member may be estimated based on an angle at which link members are connected to each other.

In addition, when a Denavit-Hartenberg (D-H) convention is used, the kinematics of the robot may include four parameters, for example, a link length a of a line member, a link offset d, a link distortion $\alpha$, and a joint angle $\theta$. In this example, when a joint rotates around a z axis, transformation matrices may be expressed as follows.

$$^0_1T = \begin{bmatrix} c\theta 1 & -c\alpha 1 s\theta 1 & s\alpha 1 s\theta 1 & 0 \\ s\theta 1 & c\alpha 1 c\theta 1 & -s\alpha 1 c\theta 1 & 0 \\ 0 & s\alpha 1 & c\alpha 1 & R \\ 0 & 0 & 0 & 1 \end{bmatrix} \quad \text{[Transformation Matrix 1]}$$

$$^1_2T = \begin{bmatrix} c\theta 2 & -c\alpha 2 s\theta 2 & s\alpha 2 s\theta 2 & 0 \\ s\theta 2 & c\alpha 2 c\theta 2 & -s\alpha 2 c\theta 2 & 0 \\ 0 & s\alpha 2 & c\alpha 2 & 0 \\ 0 & 0 & 0 & 1 \end{bmatrix} \quad \text{[Transformation Matrix 2]}$$

In Transformation Matrices 1 and 2, s denotes sine, and c denotes cosine. Through the above transformation matrices, a transformation matrix may be derived as follows.

$$^0_2T = \begin{bmatrix} c\theta 1 c\theta 2 - c\alpha 1 s\theta 1 s\theta 2 & s\alpha 1 s\alpha 2 s\theta 1 - c\alpha 2(c\alpha 1 c\theta 2 s\theta 1 + c\theta 1 s\theta 2) & c\alpha 2 s\alpha 1 s\theta 1 + s\alpha 2(c\alpha 1 c\theta 2 s\theta 1 + c\theta 1 s\theta 2) & 0 \\ c\theta 2 s\theta 1 + c\alpha 1 c\theta 1 s\theta 2 & -c\theta 1 s\alpha 1 s\alpha 2 + c\alpha 2(c\alpha 1 c\theta 1 c\theta 2 - s\theta 1 s\theta 2) & -c\theta 1(c\alpha 2 s\alpha 1 + c\alpha 1 c\theta 2 s\alpha 2) + s\alpha 2 s\theta 1 s\theta 2 & 0 \\ s\alpha 1 s\theta 2 & c\alpha 2 c\theta 2 s\alpha 1 + c\alpha 1 s\alpha 2 & c\alpha 1 c\alpha 2 - c\theta 2 s\alpha 1 s\alpha 2 & R \\ 0 & 0 & 0 & 1 \end{bmatrix}$$

[Transformation Matrix 3]

The above transformation matrix may represent a case in which two link members are provided. A point to which relocation is to be performed by a translation, an offset, a scale, or a rotation on a three-dimensional (3D) coordinate system may be estimated using the transformation matrix.

In addition, a location and direction of the emitting member or the end-effector may be expressed as follows.

$$^0_2T = \begin{bmatrix} ^0x_2 & ^0y_2 & ^0z_2 & ^0p_2 \\ 0 & 0 & 0 & 1 \end{bmatrix} \quad \text{[Transformation Matrix 4]}$$

$$^0p_2 = \begin{bmatrix} 0 \\ 0 \\ R \end{bmatrix}$$ [Transformation Matrix 5]

In this example, the location of the emitting member or the end-effector may be constantly uniform.

Figure 4:
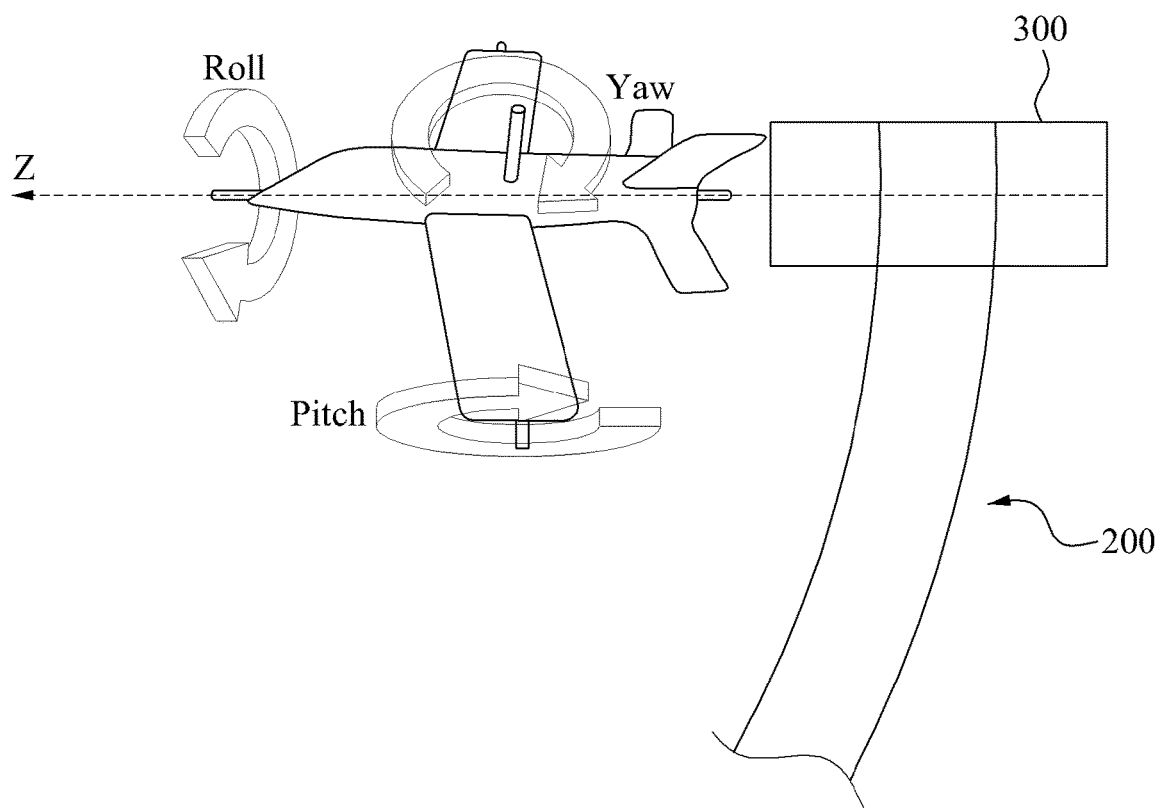
FIG. 4 illustrates a direction of an emitting member in a 3D emitting apparatus according to an embodiment of the present invention.

FIG. 4 illustrates a direction of the emitting member 300 in the 3D emitting apparatus 10. Referring to FIG. 4, the emitting member 300 may face a z axis, and have a roll movement of rotating on the z axis, a yaw movement of oscillating up and down based on the z axis, and a pitch movement of rotating up and down based on the z axis. In this example, a roll direction may be insignificant in the emitting member 300. Only a z-vector may be considered for a direction of the emitting member 300. Thus, Transformation Matrix 2 may be arranged as follows.

$$^0z_2 = \begin{bmatrix} z_1 \\ z_2 \\ z_3 \end{bmatrix} = \begin{bmatrix} c\alpha_2 s\alpha_1 s\theta_1 + \\ s\alpha_2(c\alpha_1 c\theta_2 s\theta_1 + c\theta_1 s\theta_2) - \\ c\theta_1(c\alpha_2 s\alpha_1 + c\alpha_1 c\theta_2 s\alpha_2) + \\ s\alpha_2 s\theta_1 s\theta_2 \\ c\alpha_1 c\alpha_2 - c\theta_2 s\alpha_1 s\alpha_2 \end{bmatrix}$$ [Transformation Matrix 6]

Figure 5:
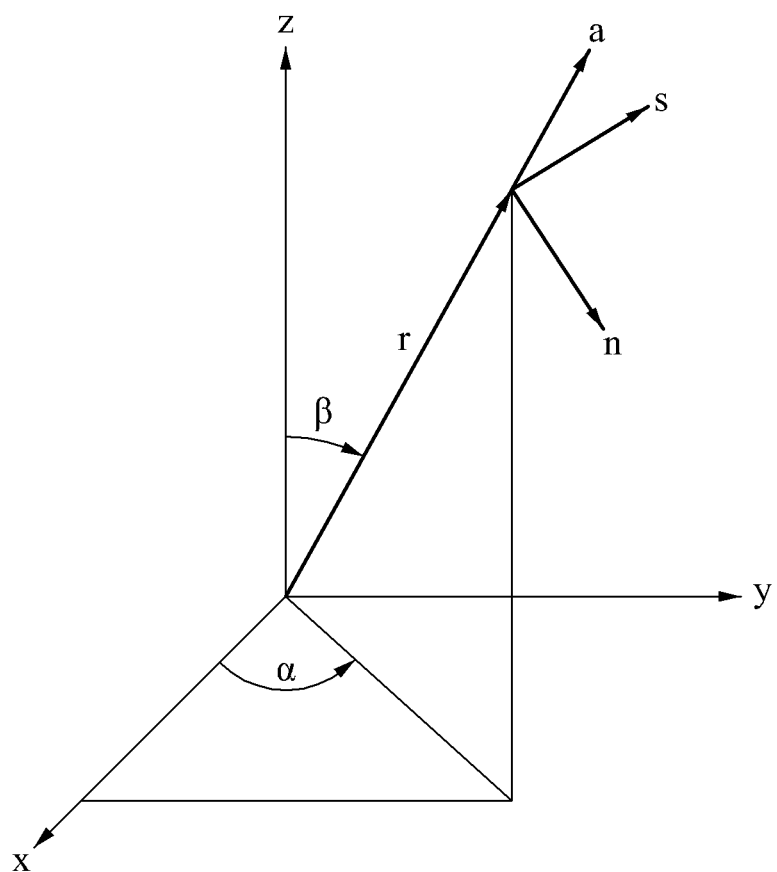
FIG. 5 illustrates spherical coordinates.

A desired direction of the emitting member 300 may be designated as spherical coordinates α and β of FIG. 5. When the direction of the emitting member 300 is given as α and β of FIG. 5, rotation matrices corresponding to the direction may be expressed as follows.

$$R_{spherical} = R_{z,\alpha}R_{y,\beta} = \begin{bmatrix} c\alpha c\beta & -s\alpha & c\alpha s\beta \\ s\alpha c\beta & c\alpha & s\alpha s\beta \\ -s\beta & 0 & c\beta \end{bmatrix}$$ [Rotation Matrix 1]

$$R_{spherical} = \begin{bmatrix} x_1 & y_1 & z_1 \\ x_2 & y_2 & z_2 \\ x_3 & y_3 & z_3 \end{bmatrix}$$ [Rotation Matrix 2]

Based on α and β from Rotation Matrices 1 and 2, $^0x_2=[x_1, x_2, x_3]^T$, $^0y_2=[y_1, y_2, y_3]^T$, and $^0z_2=[z_1, z_2, z_3]^T$ may be determined, and $\theta_1$ and $\theta_2$ may also be determined. Such a relationship may be expressed by inverse kinematics as follows.

$$\theta = f(x)^{-1}$$ [Equation 2]

In Equation 2, x denotes a vector $^0z_2=[z_1, z_2, z_3]^T$ and, θ denotes a vector including $\theta_1$ and $\theta_2$. Equation 2 may be an inverse function of Equation 1.

The joints angles $\theta_1$ and $\theta_2$ may be calculated based on orthonormal vectors $^0x_2$, $^0y_2$, and $^0z_2$. An intuitive method of calculating such vectors may be performed using spherical coordinates. When a direction is given as α and β, a rotation matrix corresponding to the direction may be expressed as follows.

$$R_{spherical} = R_{z,\alpha}R_{y,\beta} = \begin{bmatrix} c\alpha c\beta & -s\alpha & c\alpha s\beta \\ s\alpha c\beta & c\alpha & s\alpha s\beta \\ -s\beta & 0 & c\beta \end{bmatrix}$$ [Rotation Matrix 3]

In this example, constituent elements of the vectors may correspond to $^0x_2=[x_1, x_2, x_3]^T$, $^0y_2=[y_1, y_2, y_3]^T$, and $^0z_2=[z_1, z_2, z_3]^T$.

The following Equations may be extracted from Transformation Matrix 3.

$$x_3 = s\alpha_1 s\theta_2$$

$$z_3 = c\alpha_1 c\alpha_2 - c\theta_2 s\alpha_1 s\alpha_2$$ [Equation 3]

In Equation 3, $\theta_2$ may be induced as follows.

$$s\theta_2 = x_3 - s\alpha_1$$ [Equation 4]

$$c\theta_2 = \frac{z_3 + c\alpha_1 c\alpha_2}{s\alpha_1 s\alpha_2}$$

$$\tan\theta_2 = \frac{s\alpha_1 s\alpha_2(x_3 - s\alpha_1)}{z_3 + c\alpha_1 c\alpha_2}$$

$$\theta_2 = \arctan2\left(x_3 - s\alpha_1, \frac{z_3 + c\alpha_1 c\alpha_2}{s\alpha_1 s\alpha_2}\right)$$

A function arctan 2, an arctangent function including two input variables, may be used due to a stability of being close to zero input values and a characteristic of a final angle returning to an appropriate quadrant. $\theta_1$ may be calculated as follows. The following Equations 5 through 7 may be obtained from Transformation Matrix 4.

$$(x_2 = c\theta_2 s\theta_1 + c\alpha_1 c\theta_1 s\theta_2)c\alpha_1 s\theta_2$$ [Equation 5]
$$(x_1 = -s\theta_1 c\alpha_1 s\theta_2 + c\theta_1 c\theta_2)c\theta_2$$

$$c\alpha_1 s\theta_2 x_2 + c\theta_2 x_1 = c^2\alpha_1 s^2\theta_2 c\theta_1 + c^2\theta_2 c\theta_1$$ [Equation 6]

$$c\theta_1 = \frac{c\alpha_1 s\theta_2 x_2 + c\theta_2 x_1}{c_1^2 s^2\theta_2 + c^2\theta_2}$$

$$z_1 = (c\alpha_2 s\alpha_1 + s\alpha_2 c\alpha_1 c\theta_2)s\theta_1 + s\alpha_2 s\theta_2 c\theta_1$$ [Equation 7]
$$z_2 = -(c\alpha_2 s\alpha_1 + s\alpha_2 c\alpha_1 c\theta_2)c\theta_1 + s\alpha_2 s\theta_2 s\theta_1$$

In addition, the following may be assumed.

$$a = c\alpha_2 s\alpha_1 + s\alpha_2 c\alpha_1$$

$$b = s\alpha_2 s\theta_2$$ [Equation 8]

Through Equations 7 and 8, the following may be calculated.

$$a(z_1 = as\theta_1 + bc\theta_1)$$ [Equation 9]
$$b(z_2 = -ac\theta_1 + bs\theta_1)$$
$$az_1 = a^2 s\theta_1 + abc\theta_1$$
$$bz_2 = b^2 s\theta_1 - abc\theta_1$$
$$az_1 + bz_2 = (a^2 + b^2)s\theta_1$$
$$s\theta_1 = \frac{az_1 + bz_2}{a^2 + b^2}$$

Through Equations 6 and 9, $\theta_1$ may be calculated as follows.

$$\theta_1 = \arctan2\left(\frac{az_1 + bz_2}{a^2 + b^2}, \frac{c\alpha_1 s\theta_2 x_2 + c\theta_2 x_1}{c^2\alpha_1 s^2\theta_2 + c^2\theta_2}\right)$$ [Equation 10]

From Equations 4 and 10, the two joint angles $\theta_1$ and $\theta_2$ may be determined.

A Jacobian matrix will be described hereinafter.

A linear mapping between a $\theta$-space and an x-space may be as follows.

Equation 1 may be differentiated as follows.

$$^0\dot{x} = {^0}J\dot{\theta} \qquad \text{[Jacobian Matrix 1]}$$

$$^0J = \begin{bmatrix} {^0}z_0 \times ({^0}p_n - {^0}p_0) & {^0}z_1 \times ({^0}p_n - {^0}p_1) \\ {^0}z_0 & {^0}z_1 \end{bmatrix}$$

The Transformation Matrix 1 may be expressed as follows.

$$^0_1T = \begin{bmatrix} {^0}x_1 & {^0}y_1 & {^0}z_1 & {^0}p_1 \\ 0 & 0 & 0 & 1 \end{bmatrix} = \qquad \text{[Rotation Matrix 7]}$$

$$\begin{bmatrix} c\theta 1 & -c\alpha s\theta 1 & s\alpha s\theta 1 & 0 \\ s\theta 1 & c\alpha c\theta 1 & -s\alpha c\theta 1 & 0 \\ 0 & s\alpha 1 & c\alpha 1 & R \\ 0 & 0 & 0 & 1 \end{bmatrix}$$

Thus, the Jacobian matrix may be expressed as follows.

$$^0J = \begin{bmatrix} \begin{bmatrix} 0 \\ 0 \\ 1 \end{bmatrix} \times \left( \begin{bmatrix} 0 \\ 0 \\ R \end{bmatrix} - \begin{bmatrix} 0 \\ 0 \\ 0 \end{bmatrix} \right) & \begin{bmatrix} s\alpha 1 s\theta 1 \\ -s\alpha 1 c\theta 1 \\ c\alpha 1 \end{bmatrix} \times \left( \begin{bmatrix} 0 \\ 0 \\ R \end{bmatrix} - \begin{bmatrix} 0 \\ 0 \\ 0 \end{bmatrix} \right) \\ \begin{bmatrix} 0 \\ 0 \\ 1 \end{bmatrix} & \begin{bmatrix} s\alpha 1 s\theta 1 \\ -s\alpha 1 c\theta 1 \\ c\alpha 1 \end{bmatrix} \end{bmatrix} \qquad \text{[Jacobian Matrix 2]}$$

$$^0J = \begin{bmatrix} {^0}z_0 \times ({^0}p_n - {^0}p_0) & {^0}z_1 \times ({^0}p_n - {^0}p_1) \\ {^0}z_0 & {^0}z_1 \end{bmatrix} \qquad \text{[Jacobian Matrix 3]}$$

$$= \begin{bmatrix} \begin{bmatrix} 0 \\ 0 \\ 1 \end{bmatrix} \times \left( \begin{bmatrix} 0 \\ 0 \\ R \end{bmatrix} - \begin{bmatrix} 0 \\ 0 \\ 0 \end{bmatrix} \right) & \begin{bmatrix} s\alpha 1 s\theta 1 \\ -s\alpha 1 c\theta 1 \\ c\alpha 1 \end{bmatrix} \times \left( \begin{bmatrix} 0 \\ 0 \\ R \end{bmatrix} - \begin{bmatrix} 0 \\ 0 \\ 0 \end{bmatrix} \right) \\ \begin{bmatrix} 0 \\ 0 \\ 1 \end{bmatrix} & \begin{bmatrix} s\alpha 1 s\theta 1 \\ -s\alpha 1 c\theta 1 \\ c\alpha 1 \end{bmatrix} \end{bmatrix}$$

$$= \begin{bmatrix} \begin{bmatrix} 0 \\ 0 \\ 0 \end{bmatrix} & \begin{bmatrix} 0 \\ 0 \\ 0 \end{bmatrix} \\ \begin{bmatrix} 0 \\ 0 \\ 1 \end{bmatrix} & \begin{bmatrix} s\alpha 1 s\theta 1 \\ -s\alpha 1 c\theta 1 \\ c\alpha 1 \end{bmatrix} \end{bmatrix}$$

Thus, the Jacobian matrix may be expressed as follows.

$$J = \begin{bmatrix} 0 & s\alpha 1 s\theta 1 \\ 0 & -s\alpha 1 c\theta 1 \\ 1 & c\alpha 1 \end{bmatrix} \qquad \text{[Jacobian Matrix 4]}$$

Through Jacobian Matrix 4, when only an angular velocity is considered and a translational velocity is not considered, a singularity may not be achieved except for a case in which $\alpha = n\pi$ and $n \in N$ are satisfied.

As described above, a relationship between a motion of a link member and a motion of an emitting member may be expressed through a Jacobian matrix.

In detail, a location of the emitting member may be estimated based on a current location of a link member. Conversely, to enable the emitting member to face a central point or a target, an operation of a link member may be controlled based on a current location of the emitting member.

Furthermore, when a plurality of robot arms is provided, the plurality of robot arms may be controlled to operate collaboratively through a Jacobian matrix.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A three-dimensional (3D) emitting apparatus comprising:
   a table on which an object is to be disposed;
   a robot arm disposed above or below the table to perform a task on the object;
   an emitting member provided at an end portion of the robot arm; and
   a controller to control an operation of the robot arm or a position of the emitting member,
   wherein the table and the robot arm move relatively in a vertical or horizontal direction to move the object to a target point, the emitting member moves along a trajectory of rotation of the robot arm, and the trajectory of rotation is provided in a form of a concentric sphere having a center at which the target point is disposed,
   wherein the robot arm comprises a plurality of link members and a plurality of drive members, each drive member arranged to transmit a torque to a respective one of the link members,
   wherein the link members are disposed on concentric spheres having an identical center disposed at the target point and spaced apart from each other radially on the concentric spheres,
   wherein a plurality of robot arms is provided, the plurality of robot arms rotate independently and incoherently relative to one other,
   wherein a plurality of link members included in robot arms disposed far away from the target point, among the plurality of robot arms, is disposed on a greater concentric sphere than a plurality of link members included in robot arms disposed close to the target point, among the plurality of robot arms, such that collisions among the plurality of robot arms are prevented during concurrent rotations,
   wherein a plurality of emitting members corresponding to a number of the robot arms are provided, the plurality of emitting members aims at the target point in a contactless manner, and the plurality of emitting members moves on different spheres along trajectories of rotation of the plurality of robot arms, and wherein angle adjustment elements are provided at the plurality of emitting members or end portions of the plurality of robot arms to adjust angles at which the plurality of emitting members face the target point.

2. The 3D emitting apparatus of claim 1, wherein extension lines of axes of the drive members are positioned at the center.

3. The 3D emitting apparatus of claim 1, wherein
the 3D emitting apparatus is configured in a form of a cyberknife that emits radiation from the emitting member toward the object.

4. The 3D emitting apparatus of claim 1, further comprising:
an image sensor to convert light emitted from the emitting member and reflected by the object into an electrical image signal; and
a data processor to generate a 3D image by combining a plurality of images received from the image sensor,
wherein the 3D emitting apparatus is configured in a form of a 3D scanner that acquires a 3D shape of the object.

5. The 3D emitting apparatus of claim 1, wherein the object is provided using a fluid material comprising an ink, an ultraviolet ray is emitted from the emitting member, and the 3D emitting apparatus is configured in a form of a 3D printer that irradiates the ultraviolet ray toward the object to harden the object.

6. The 3D emitting apparatus of claim 1, wherein the robot arm comprises:
a first central member;
a first link member to rotate on a longitudinal axis of the first central member;
a first drive member disposed at one end of the first link member to transmit a torque to the first link member;
a second link member connected to another end of the first link member to rotate on a first axis; and
a second drive member disposed between the first link member and the second link member to transmit a torque to the second link member.

7. The 3D emitting apparatus of claim 6, wherein the robot arm further comprises:
a third link member connected to a portion of the first central member, the portion differing from a portion to which the first link member is connected, to rotate on the longitudinal axis of the first central member;
a third drive member disposed at one end of the third link member to transmit a torque to the third link member;
a fourth link member connected to another end of the third link member to rotate on a second axis; and
a fourth drive member disposed between the third link member and the fourth link member to transmit a torque to the fourth link member.

8. The 3D emitting apparatus of claim 7, wherein the robot arm further comprises:
a second central member disposed on an axis identical to the longitudinal axis of the first central member and spaced apart from the center by a distance corresponding to a distance between the first central member and the center;
a fifth link member to rotate on a longitudinal axis of the second central member;
a fifth drive member disposed at one end of the fifth link member to transmit a torque to the fifth link member;
a sixth link member connected to another end of the fifth link member to rotate on a third axis; and
a sixth drive member disposed between the fifth link member and the sixth link member to transmit a torque to the sixth link member.

9. The 3D emitting apparatus of claim 8, wherein the robot arm further comprises:
a seventh link member connected to a portion of the second central member, the portion differing from a portion to which the fifth link member is connected, to rotate on the longitudinal axis of the second central member;
a seventh drive member disposed at one end of the seventh link member to transmit a torque to the seventh link member;
an eighth link member connected to another end of the seventh link member to rotate on a fourth axis; and
an eighth drive member disposed between the seventh link member and the eighth link member to transmit a torque to the eighth link member.

10. The 3D emitting apparatus of claim 9, wherein the longitudinal axis of the first central member, the longitudinal axis of the second central member, the first axis, the second axis, the third axis, and the fourth axis are positioned at the center.

11. The 3D emitting apparatus of claim 9, wherein the first axis, the second axis, the third axis, and the fourth axis are formed to be perpendicular to tangential directions of end portions of the first link member, the second link member, the third link member, the fourth link member, the fifth link member, the sixth link member, the seventh link member, and the eighth link member.

12. The 3D emitting apparatus of claim 9, wherein the first link member and the second link member are disposed farther away from the center than the third link member and the fourth link member, and the fifth link member and the sixth link member are disposed farther away from the center than the seventh link member and the eighth link member.

13. The 3D emitting apparatus of claim 7, wherein, when the third link member is disposed between the first link member and the second link member, each of lengths of the third link member and the fourth link member is shorter than a length of the first link member.

14. The 3D emitting apparatus of claim 13, wherein the third link member and the fourth link member are disposed closer to the center than the second link member, and the fourth link member is disposed closer to the center than the third link member.

15. The 3D emitting apparatus of claim 9, wherein, when the seventh link member is disposed between the fifth link member and the sixth link member, lengths of the seventh link member and the eighth link member are shorter than a length of the fifth link member.

16. The 3D emitting apparatus of claim 15, wherein the seventh link member and the eighth link member are disposed closer to the center than the sixth link member, and the eighth link member is disposed closer to the center than the seventh link member.

17. The 3D emitting apparatus of claim 9, wherein the emitting member is disposed to be perpendicular to tangential directions of end portions of the second link member, the fourth link member, the sixth link member, and the eighth link member.

18. The 3D emitting apparatus of claim 1, further comprising:
  a position adjustment element to adjust a position of the table.

\* \* \* \* \*